(12) United States Patent
Hartwell

(10) Patent No.: US 8,480,698 B2
(45) Date of Patent: Jul. 9, 2013

(54) WASTE CONTROL APPARATUS

(75) Inventor: Edward Hartwell, York (GB)

(73) Assignee: Smith & Nephew, Inc., Memphis, TN (US)

( * ) Notice: Subject to any disclaimer, the term of this patent is extended or adjusted under 35 U.S.C. 154(b) by 152 days.

(21) Appl. No.: 12/808,471

(22) PCT Filed: Nov. 12, 2008

(86) PCT No.: PCT/GB2008/051054
§ 371 (c)(1),
(2), (4) Date: Jun. 16, 2010

(87) PCT Pub. No.: WO2009/081176
PCT Pub. Date: Jul. 2, 2009

(65) Prior Publication Data
US 2010/0280536 A1    Nov. 4, 2010

(30) Foreign Application Priority Data
Dec. 20, 2007 (GB) .................................. 0724836.2

(51) Int. Cl.
*A61B 17/32* (2006.01)
(52) U.S. Cl.
USPC ............................................ 606/167; 604/22
(58) Field of Classification Search
USPC .................... 606/167, 180; 604/22, 27, 58
See application file for complete search history.

(56) References Cited

U.S. PATENT DOCUMENTS 6,030,399 A * 2/2000 Ignotz et al. .................. 606/167
2002/0045912 A1 4/2002 Ignotz
2004/0092920 A1 5/2004 Rozenshpeer

FOREIGN PATENT DOCUMENTS

ES     2 091 698        11/1996
WO    WO 03/045259      6/2003

OTHER PUBLICATIONS

International Search Report for PCT/GB2008/051054, mailed May 8, 2009, 3 pages.
International Preliminary Report on Patentability for International Application No. PCT/GB2008/051054 issued Jun. 22, 2010.

* cited by examiner

*Primary Examiner* — Victor Nguyen
(74) *Attorney, Agent, or Firm* — Fish & Richardson P.C.

(57) ABSTRACT

Liquid jet surgical cutting apparatus (10) and a method of use thereof are described, the apparatus including a fluid reservoir (12) containing a supply of cutting fluid (14), a pump (16) to supply the cutting fluid to a liquid jet surgical cutting instrument, a liquid jet surgical cutting instrument (20), and a drain conduit (22) to receive and drain waste cutting fluid (14) and entrained debris wherein the drain conduit is operably connected to a waste canister (24), the waste canister having a vacuum generator (26) operably connected thereto to apply a vacuum to an interior of the waste canister and to the drain conduit.

9 Claims, 2 Drawing Sheets

WASTE CONTROL APPARATUS

Figure 1:
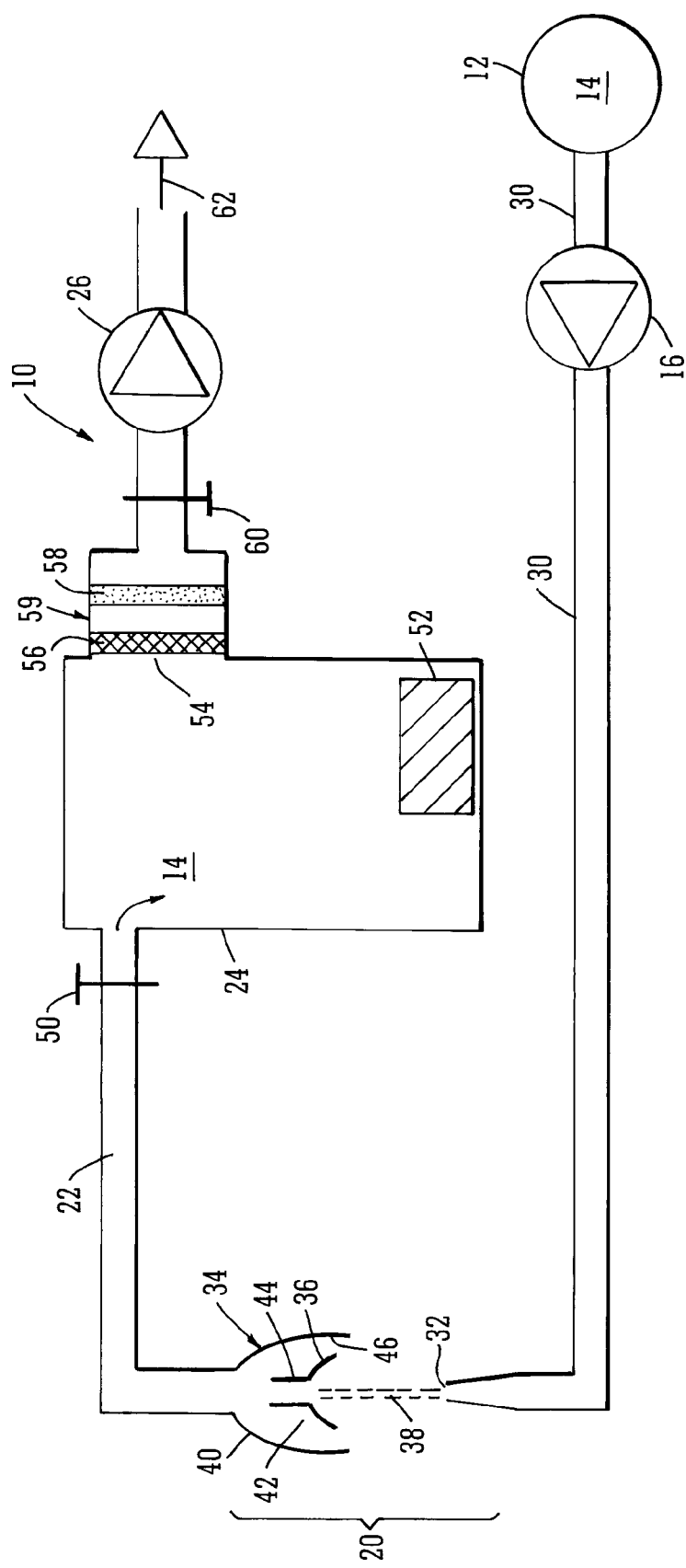

The present invention relates to a method and apparatus for dealing with waste produced particularly, though not exclusively, by liquid jet surgical instrument cutting apparatus Recent surgical techniques have made use of so-called water scalpels where a fine jet of liquid at very high pressure is used to effect tissue cutting and/or removal in place of sharp edged scalpels. The apparatus employed with such high pressure jet cutting systems generally comprises a reservoir containing sterile cutting liquid such as saline solution, for example, a high pressure pump which supplies the cutting fluid to a hand-held cutting instrument which generally has a drain conduit which captures the high pressure jet after cutting to carry away waste cutting fluid and tissue debris, for example, from a surgical procedure being carried out by means of a vacuum created by a venturi effect of the liquid jet entering an aperture of a venturi arrangement in the entrance of the drain conduit in the hand-held instrument.

An example of a liquid jet surgical cutting instrument is described in WO 2003/045259, the content of which is included herein by reference.

A problem with existing systems of liquid jet surgical cutting apparatus is that when the water cutting jet is stopped, the venturi effect and consequently the vacuum ceases and the debris contained in the drain conduit may remain until the liquid jet is started again. If the hand-held instrument is allowed to fall into a downwardly orientated position, waste debris can drip on the floor of an operating theatre and result in a potential biohazard. Even if the hand-held instrument is not allowed to adopt an attitude where waste debris can drip on the floor, restarting of the water jet can cause spray and rebound until the drain conduit has cleared following restarting of the liquid jet. Furthermore, waste can back-up in the drain conduit due to coiling thereof or blockage by too much debris.

It is an object of the present invention to minimise or obviate the problems of prior art liquid jet surgical cutting instrument apparatus.

According to a first aspect of the present invention there is provided liquid jet surgical cutting apparatus, the apparatus comprising: a fluid reservoir containing a supply of cutting fluid; a pump to supply the cutting fluid to a liquid jet surgical cutting instrument; a liquid jet surgical cutting instrument; a drain conduit to receive and drain waste cutting fluid and entrained debris wherein the drain conduit is operably connected to a waste canister, the waste canister having vacuum means operably connected thereto to apply a vacuum to an interior of the waste canister and to said drain conduit.

The present invention provides a vacuum to the waste canister and drain conduit so that a continuous draining impetus by the vacuum is applied to the drain conduit independently of whether the liquid cutting jet is flowing or not. Alternatively, the vacuum means can be controlled so that it runs for a period of time after the liquid jet has been stopped so that any remaining waste cutting fluid and entrained debris is carried away from the drain conduit into the waste canister.

The vacuum means can be any suitable type of vacuum pump such as an electrically powered vacuum pump, for example, or may be an off-take of a suitable permanently installed vacuum system in a hospital, for example.

Desirably the waste canister has suitable filter means such as hydrophobic filters and bacterial filters associated with an outlet port of the waste canister between the waste canister and vacuum means to prevent the exhaust and spread of bacteria. Such an arrangement also protects the vacuum means from bioburden.

Filters may also include an odour filter.

The waste canister may be connected and/or disconnected form the drain conduit by suitable valve means.

The waste canister may also be provided with a gelling agent or other means to solidify the contained waste to render the collected waste a solid to reduce slopping thereof and to facilitate subsequent disposal.

The waste canister may have a portion of tubing between the drain conduit and the waste canister to receive a clamp to seal off the tubing when the waste canister is full and requires disposal.

Alternatively to clamps, connection valves in the form of, for example, non-return valves, manual shut-off valves or auto-shut-off valves may be employed to disconnect and seal off the waste container when full.

In an embodiment of the apparatus according to the present invention the waste canister may be provided with a port for the attachment of pressure monitoring means thereto. A second pressure monitoring means may be provided at a position between filters on a fluid exit port from the waste canister and vacuum pump means, for example. A drop in the vacuum indicated to exist in the waste canister relative to that registered by the second pressure monitoring means may indicate that the canister is full and requires changing. On the other hand a relatively high indicated vacuum in the waste canister and at the second pressure monitoring means may indicate that the drain conduit is kinked or otherwise blocked and that waste fluid is failing to be drawn into the waste canister.

According to a second aspect of the present invention there is provided a method of using liquid jet surgical cutting apparatus, the method comprising the steps of: providing a fluid reservoir containing a supply of cutting fluid; providing a pump to supply the cutting fluid to a liquid jet surgical cutting instrument; providing a liquid jet surgical cutting instrument; providing a drain conduit to receive and drain waste cutting fluid and entrained debris; the method further comprising the step of operably connecting the drain conduit to a waste canister and providing the waste canister with vacuum means operably connected to the waste canister to apply a vacuum to an interior of the waste canister and to said drain conduit.

The method may include the step of operating the vacuum means for all of the time whilst a surgical procedure is being carried out or may alternatively include the step of delaying cessation of the operation of the vacuum means until a predetermined time after a liquid cutting jet has been stopped in order to ensure that the drain conduit is emptied of waste cutting fluid and debris prior to a liquid cutting jet being re-established.

The method may also include the step of providing pressure sensing means associated with the waste canister and/or the vacuum pump to determine whether the waste canister is full or if there is a fault which may need rectification.

Figure 2:
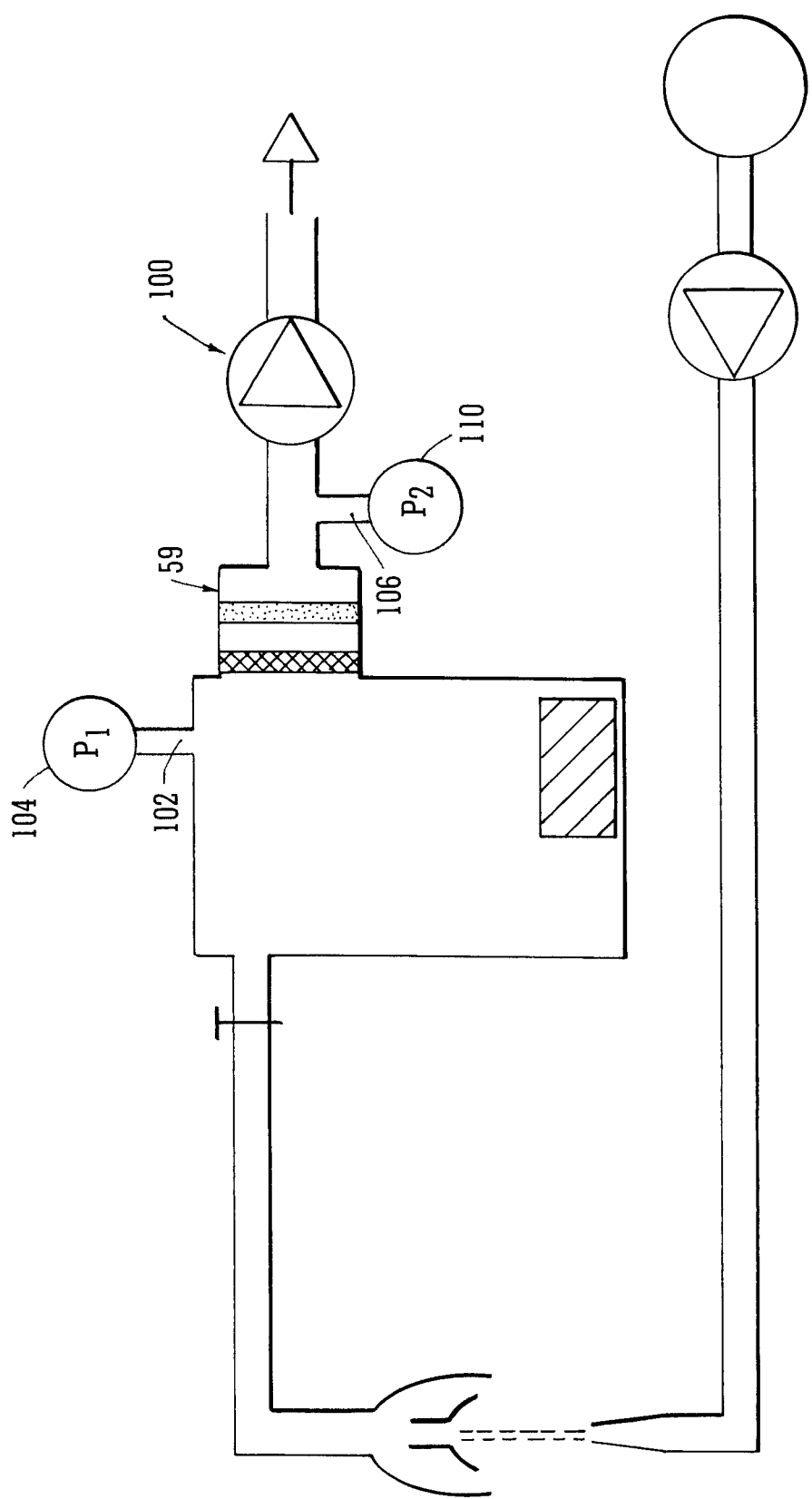

In order that the present invention may be more fully understood, examples will now be described by way of illustration only with reference to the accompanying drawings, of which:

FIG. 1 shows a schematic view of apparatus according to a first embodiment of the present invention; and FIG. 2 shows a schematic representation of apparatus according to a second embodiment of the present invention.

Referring now to the drawings and where the same features have the same reference numerals.

FIG. 1 shows a schematic representation of a first embodiment 10 of apparatus according to the present invention. The apparatus comprises: a reservoir 12 containing a supply of liquid jet cutting fluid 14; a high pressure pump 16 to supply the fluid 14 to a hand-held liquid jet surgical cutting instrument 20; a drain conduit 22; a waste canister 24; and a vacuum pump 26. In FIG. 1 the reservoir 12, pump 16 and liquid jet surgical cutting instrument are connected by a conduit 30. The liquid jet surgical cutting instrument is described only by its functional features (with respect to the drainage system) of jet nozzle 32 and venturi ejector assembly 34 which comprises a venturi port 36 into which a high pressure liquid jet 38 is directed from the nozzle 32 and which venturi port 36 is surrounded by shroud 40. In the space 42 between the outer surface 44 of the venturi port 36 and the inner surface 46 of the shroud 40, a vacuum is generated due to the flowing liquid cutting jet 38 and which vacuum causes the waste cutting fluid 14 and debris (not shown) resulting from a surgical procedure in operation to be drawn into both the venturi port and into the drain conduit 22. The drain conduit 22 is connected to the waste canister 24 by a shut-off valve 50 which enables the waste canister to be disconnected for disposal. The waste canister is also provided with a gelling agent 52 to render incoming waste fluid 14 (and debris) solid. The waste canister has an outlet port 54 for gaseous fluid and a hydrophobic filter 56 and an anti-bacterial filter 58 (an odour filter may also be employed—not shown) in a housing 59 connected to the port 54 to prevent liquid and bacteria from being drawn out of the waste canister 24 by the vacuum pump 26. The vacuum pump 26 is connected by a second shut-off valve 60 so that the vacuum pump may be re-used after disposal of a filled waste canister 24. Exhaust 62 from the vacuum pump may be effected through suitable filters and a silencing system (not shown).

In operation, the vacuum pump 26 creates a vacuum in the waste canister 24 and drain conduit 22 which vacuum assists in the flow of waste cutting fluid 14 and debris from the ejector assembly 34 through the conduit 22 and into the waste canister 24. The vacuum pump 26 may be operated all the time that the surgical procedure is in progress so that irrespective of whether the fluid jet 38 is in existence there is always a fluid flow from the ejector assembly along the conduit 22 into the waste canister 24. Thus, this method of operation ensures that the drain conduit 22 is empty at all times.

Alternatively, the vacuum pump may be made to continue operation for a predetermined period of time after cessation of the liquid jet 38 which is produced by the high pressure pump 16. Thus a control system (not shown) governing the operation of the high pressure pump 16 and vacuum pump 26 may be integrated so as to effect a delay between the high pressure pump 16 stopping or the jet 38 stopping and the vacuum pump 26 stopping. Thus, the drain conduit 22 will always be emptied following cessation of the liquid jet 38.

FIG. 2 shows a similar system of apparatus 100 to that of FIG. 1 but of a second embodiment of the present invention. In this embodiment the basic apparatus features of FIG. 1 are still present and function in the same manner but the apparatus further includes a port 102 on the waste canister the port 102 receiving a pressure gauge 104 and a suitable connection 106 between the filter housing 59 and vacuum pump 26 to receive a second pressure gauge 110. The purpose of the two pressure gauges is to indicate when the waste canister 24 may be full or if there may be another potential problem with the drainage system. For example, if the pressure gauge 104 indicates a significantly lower vacuum level than gauge 110 then a full canister is indicated. If, however, both the two pressure gauges 104, 110 indicate a relatively higher pressure than would be expected and substantially equal vacuum then a kinked or otherwise blocked drainage conduit 22 is indicated and appropriate action may be taken. Generally, the two pressure gauges 104, 110 may be part of a more comprehensive control system (not shown) which may provide for automated alarms and shutdowns and the like in the event of malfunction of the equipment or in the case of an indicated full waste container.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

The invention claimed is:

1. Liquid jet surgical cutting apparatus, the apparatus comprising:
    a fluid reservoir containing a supply of cutting fluid;
    a liquid jet surgical cutting instrument;
    a pump configured to supply the cutting fluid to the liquid jet surgical cutting instrument;
    a drain conduit to receive and drain waste cutting fluid and entrained debris, wherein the drain conduit is operably connected to a waste canister, the waste canister having a vacuum generator operably connected thereto to apply a vacuum to an interior of the waste canister and to said drain conduit, the waste canister also having a filter on an outlet port thereof;
    a first pressure sensor operably connected to an interior of the waste canister, the first pressure sensor being configured to measure a pressure inside said waste canister; and
    a second pressure sensor operably connected intermediate said filter and said vacuum generator, the second pressure sensor being configured to measure a pressure between said filter and said vacuum generator.

2. Liquid jet surgical cutting apparatus according to claim 1 wherein the vacuum generator is an electrically powered vacuum pump.

3. Liquid jet surgical cutting apparatus according to claim 1 wherein the filter comprises at least one selected from the group comprising hydrophobic, odor, and anti-bacterial filters.

4. Liquid jet surgical cutting apparatus according to claim 1 wherein the waste canister is connected to the drain conduit by a valve.

5. Liquid jet surgical cutting apparatus according to claim 1 wherein the waste canister has a gelling agent.

6. A method of using liquid jet surgical cutting apparatus, the method comprising the steps of:
    providing a fluid reservoir containing a supply of cutting fluid;
    providing a pump to supply the cutting fluid to a liquid jet surgical cutting instrument;
    providing a liquid jet surgical cutting instrument; and
    providing a drain conduit to receive and drain waste cutting fluid and entrained debris; the method further comprising the steps of:
    operably connecting the drain conduit to a waste canister and providing the waste canister with a vacuum generator operably connected to the waste canister to apply a vacuum to an interior of the waste canister and to said drain conduit, providing said waste canister with a filter in an outlet port thereof, providing a first pressure sensor operably connected to an interior of said waste canister to thereby measure a pressure inside said waste canister, and providing a second pressure sensor operably connected intermediate said filter and said vacuum generator to thereby measure a pressure between said filter and said vacuum generator.

7. A method according to claim 6 including the further step of operating the vacuum generator for all of the time while a surgical procedure is being carried out.

8. A method according to claim 6 including the further step of delaying cessation of the operation of the vacuum generator until a predetermined time after a liquid cutting jet has been stopped.

9. A method according to claim 6 further including the step of measuring a pressure differential between said first and said second pressure sensor to determine a waste canister full condition.

\* \* \* \* \*

UNITED STATES PATENT AND TRADEMARK OFFICE
CERTIFICATE OF CORRECTION

PATENT NO. : 8,480,698 B2  Page 1 of 1
APPLICATION NO. : 12/808471
DATED : July 9, 2013
INVENTOR(S) : Edward Hartwell It is certified that error appears in the above-identified patent and that said Letters Patent is hereby corrected as shown below:

In the claims

At Col. 4, line 44, (Claim 2, line 1), replace "Liquid" with --The liquid--.

At Col. 4, line 47, (Claim 3, line 1), replace "Liquid" with --The liquid--.

At Col. 4, line 51, (Claim 4, line 1), replace "Liquid" with --The liquid--.

At Col. 4, line 54, (Claim 5, line 1), replace "Liquid" with --The liquid--.

At Col. 5, line 13, (Claim 7, line 1), replace "A method" with --The method--.

At Col. 5, line 16, (Claim 8, line 1), replace "A method" with --The method--.

At Col. 5, line 20, (Claim 9, line 1), replace "A method" with --The method--.

Signed and Sealed this
Fifth Day of January, 2016

Michelle K. Lee
*Director of the United States Patent and Trademark Office*